US006432547B1

(12) United States Patent
Kroll et al.

(10) Patent No.: US 6,432,547 B1
(45) Date of Patent: Aug. 13, 2002

(54) BREATHABLE FILM LAYER COMPOSITIONS

(75) Inventors: Mark S. Kroll, Arden Hills; Greg J. Van Lith, Stillwater, both of MN (US)

(73) Assignee: H.B. Fuller Licensing & Financing Inc., St. Paul, MN (US)

( * ) Notice: Subject to any disclaimer, the term of this patent is extended or adjusted under 35 U.S.C. 154(b) by 0 days.

(21) Appl. No.: 09/503,994

(22) Filed: Feb. 14, 2000

Related U.S. Application Data

(60) Provisional application No. 60/121,098, filed on Feb. 22, 1999.

(51) Int. Cl.[7] ............................. B32B 27/34; B32B 27/30
(52) U.S. Cl. ..................... 428/474.4; 428/480; 428/522; 524/310; 524/377
(58) Field of Search .................... 524/310, 377; 428/474.4, 480, 522

(56) References Cited

U.S. PATENT DOCUMENTS

| 4,899,521 A | * | 2/1990 | Havens ........................ 53/461 |
| 5,149,333 A | * | 9/1992 | Sasse ........................ 604/367 |
| 5,756,651 A | * | 5/1998 | Chen et al. ................. 528/354 |

FOREIGN PATENT DOCUMENTS

| EP | 0 890 350 A1 | 1/1999 |
| EP | 0 963 760 A1 | 12/1999 |
| EP | 0 963 837 A1 | 12/1999 |
| EP | 0 964 026 A1 | 12/1999 |

* cited by examiner

Primary Examiner—D. S. Nakarani
(74) Attorney, Agent, or Firm—Allison A. Johnson, P.A.

(57) ABSTRACT

The present invention is directed to compositions that are useful for forming breathable film layers and articles constructed therefrom. The composition comprises at least one thermoplastic polymer compounded with at least one diluent or a radiation curable composition. The composition is impermeable to fluids and exhibits a water vapor transmission rate of at least 100 $g/m^2$/day.

26 Claims, No Drawings

BREATHABLE FILM LAYER COMPOSITIONS

CROSS-REFERENCE TO RELATED APPLICATION

This application is a continuation of U.S. Provisional Application Serial No. 60/121,098 filed on Feb. 22, 1999.

FIELD OF THE INVENTION

The present invention relates to compositions that are useful for forming a breathable fluid impermeable barrier layer. The breathable film layer finds utility in durable goods such as tents, footwear, rainwear, etc., as well as for absorbent disposable articles such as disposable diapers, feminine napkins, and medical devices and dressings. The compositions are preferably applied as a continuous film with a non-contact coating method.

SUMMARY OF THE INVENTION

The present invention is directed to compositions that are useful for forming breathable film layers and articles constructed therefrom. The composition comprises at least one thermoplastic polymer compounded with at least one diluent or a radiation curable composition. The composition is impermeable to fluids and exhibits a water vapor transmission rate of at least 100 g/m²/day.

In one embodiment, the present invention relates to a composition comprising from about 10 wt-% to about 75 wt-% of at least one breathable thermoplastic polymer and from about 25 wt-% to about 90 wt-% of at least one diluent. In a preferred embodiment, the breathable thermoplastic polymer is water sensitive. In another preferred embodiment, the breathable thermoplastic polymer is a methacrylic acid copolymer. In a most preferred embodiment, the breathable thermoplastic polymer is a polyether block amide. The diluent is a plasticizer, wax, tackifying resin or mixture thereof and preferably a plasticizer having ether or alcohol oxygen linkages such as polyethylene glycol.

DETAILED DESCRIPTION OF THE INVENTION

By "breathable" it is meant that the composition allows for the passage of moisture vapor. The preferred water vapor transmission rate (WVTR) depends on the end-use application. However, in the context of the present invention, "breathable" refers to a WVTR of at least 100 g/m²/day as measured in accordance with ASTM E96 for a 40 μm to 50 μm coating.

By "impermeable" it is meant that the composition does not allow for the passage of fluids at a pressure of 10 psi. This terminology is clarified as needed throughout the description. For example, the Eastman AQ copolyesters are body fluid (saline solution) impermeable, yet water soluble (permeable).

The present invention employs a thermoplastic composition comprising at least one thermoplastic polymer and at least one diluent or a radiation responsive composition.

The thermoplastic compositions are particularly useful for forming a continuous fluid impermeable barrier layer. However, in many embodiments the compositions are also suitable for use as hot melt adhesives. Preferably, the barrier layer is formed in accordance with the method described in U.S. Pat. No. 5,827,252 issued Oct. 27, 1998, incorporated herein by reference.

In accordance with U.S. Pat. No. 5,827,252, the thermoplastic composition is relatively low in viscosity in comparison to typical film grade materials. Accordingly, the thermoplastic composition exhibits certain Theological characteristics, preferably falling within a rheological window. The complex viscosity at high shear rates, for example at about 1,000 radians/second, is less than about 500 poise. The complex viscosity at low shear rates, for example at less than about 1 radian/second, ranges from about 100 poise to about 1,000 poise. Thermoplastic compositions having a wide window of application are those which exhibit the appropriate rheological properties at a variety of application conditions, particularly at low temperatures. The desired Theological properties are preferably obtained at temperatures less than about 180° C., more preferably at temperatures less than about 160° C., even more preferably at temperatures less than 140° C., and most preferably at temperatures less than about 120° C.

The barrier layer may be of a conventional film thickness, for example from about 0.8 to about 2 mils. Alternatively, the barrier layer may advantageously be very thin, employing a coating weight thickness from about 1 g/m² to about 10 g/m². For embodiments wherein the barrier layer is very thin or for embodiments that employ a composition which is not radiation curable, the barrier layer is typically of low film strength, obtaining its tear resistance from the substrate it is coated to. However, for embodiments employing a radiation curable system or higher coating thicknesses, the barrier layer alone may exhibit sufficient film strength to be self-supporting, particularly for disposable absorbent article applications.

The resulting barrier layer is impermeable to (body) fluid and is characteristically breathable. Breathability is expressed as a function of water vapor transmission rate (WVTR) measured in accordance with ASTM E-96 for a 40–50 μm barrier layer coating on porous nonwoven or of a neat barrier film layer in the case of self-supporting film layers. The barrier layer has a water vapor transmission rate of at least about 100 g/m²/day, preferably at least 200 g/m²/day, more preferably at least 400 g/m²/day, even more preferably at least 800 g/m²/day and most preferably from about 1000 to 2000 g/m²/day or higher.

In the case of compositions that are not intended to be radiation cured, the breathable composition of the present invention comprises at least one thermoplastic polymer and at least one diluent. The thermoplastic polymer, the diluent, or both are sufficiently breathable such that the formulated composition exhibits the desired WVTR rate.

The term "polymer" refers to a component having a Mw greater than about 3000 and preferably greater than about 10,000. In embodiments wherein the thermoplastic polymer employed has a high moisture vapor transmission rate, the diluent is sufficiently compatible with the thermoplastic polymer but need not be breathable. However, for embodiments wherein the thermoplastic polymer is not sufficiently breathable, the diluent preferably contributes to the breathability of the mixture. The thermoplastic polymer is typically polar in nature and may also be described as breathable, water sensitive including water swellable, water soluble or water dispersible, or biodegradable.

Consistent with the definition of breathable thermoplastic compositions, breathable thermoplastic polymers are those having a WVTR water vapor transmission rate of at least about 100 g/m²/day, preferably at least 200 g/m²/day, more preferably at least 400 g/m²/day, even more preferably at least 800 g/m²/day and most preferably from about 1000 to 2000 g/m²/day or higher. Breathable polymers typically contain low reactivity oxygen linkages. The oxygen linkages are preferably along the polymer backbone, as in the case of polyesters and polyethers. However, terminal low reactivity oxygen linkages may also contribute breathability as in the case of long chain (high molecular weight) polyols, as well as hydroxylated and epoxidized thermoplastic compounds. Additionally, the applicants surmise that certain thermoplastic polymers containing silicone-oxygen linkages such as siloxane may also be suitable. Particularly in the case of employing polymers having terminal oxygen linkages, care should be taken in selecting the additional ingredients in the thermoplastic mixture to insure such ingredients will not react.

Representative examples of breathable polymers include linear saturated polyesters such as Dynapol or Dynacoll polymers from Creanova Inc, (Piscataway, N.J.), polyether block amide and polyester ether block copolymers available from Elf Atochem (Birdsboro, Pa.) as PEBAX or Hoechst Celanese (Dallas, Tex.) as RITE-FLEX respectively. Within each class of polymers, the most preferred polymers are generally those exhibiting the highest degree of gas permeability such as PEBAX 2533 SN01 and PEBAX 3533 SN 01.

The breathable thermoplastic composition of the present invention may comprise one or more water sensitive thermoplastic polymers. However, since these materials are characteristically swellable, dispersible, or soluble in water, these materials typically lack the water impermeability properties required for use as a fluid impermeable barrier layer. Hence, in one embodiment, the present invention is directed to reducing the water sensitivity of such materials to improve the water impermeability. Water sensitive polymers useful herein include a variety of crystalline and amorphous water soluble and/or water dispersible polymers and preferably a blend of a crystalline water soluble polyamide and an amorphous water sensitive polymer.

Water soluble polyamides are the reaction product of at least one polyoxyalkylene diamine with at least one dicarboxylic acid or esters thereof.

The polyoxyalkylene glycol diamine has the formula:

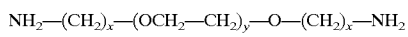

wherein X ranges from 2 to 3 and Y ranges from 1 to 2.

Representative examples include triethylene glycol diamine, wherein X=2 and Y=1, and tetraethylene glycol diamine, wherein X=2 and Y=2. Commercial diamines include Jeffamine® XTJ-504 amine and Jeffamine® EDR-192 amine available from Huntsman Chemical Co., Houston, Tex. A preferred diamine is 4,7,10-trioxatridecane-1,13-diamine (TTD diamine) available from BASF, Parsippany, N.J., wherein X=3 and Y=2. Other amines such as Jeffamine® D-230, D-400, XTJ-500, XTJ-501 and XTJ-502 are also useful provided a chain terminator acid or amine is employed during the reaction, and/or additional ingredients such as waxes, tackifiers, crystalline polymers, and monoacids are subsequently combined with the reacted polyamide. For example, when adipic acid is reacted with TTD diamine and Jeffamine® D-230, the resulting polyamide is relatively slow setting with respect to reacting adipic acid with TTD diamine alone.

The polyoxyalkylene diamine is reacted with an equal stoichiometric ratio of a dicarboxylic acid. Suitable dicarboxylic acids are those having from 5 to 36 carbon atoms including adipic acid, pimelic acid, azelaic acid, sebacic acid, suberic acid, dodecanedioic acid, terephthalic acid, isophthalic acid, t-butyl isophthalic acid, dimer acid and mixtures thereof. The esters and anhydrides of these acids may also be used. Adipic acid is preferred.

The resulting water soluble polyether amide preferably has a melt point about 190° C. or less as in the case when adipic acid is reacted with Jeffamine® XTJ-504. More preferably, the melt point is about 155° C. or less as in the case when adipic acid is reacted with Jeffamine® EDR-192. The most preferred water soluble polyether amide has a melt point of about 150° C. or less as in the case when adipic acid is reacted with TTD diamine. This particular combination results in a faster setting, strong, easily processed water soluble polyether amide. The low melt temperature makes this combination particularly attractive for low application temperature applied hot melt adhesives or barrier layers having an application temperature less than 177° C.

Certain polyamides are preferred due to their contribution to the nonblocking and humidity resistant properties. Polyamides exhibiting such properties are those which are produced by reacting polyoxyalkylene diamine with at least one dicarboxylic acid or an ester thereof, the polyoxyalkylene diamine having the formula:

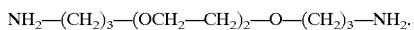

In this embodiment, adipic acid is the preferred dicarboxylic acid. However, other diacids may also be employed provided the mole percent of the additional diacids is about 10 mole percent or less with respect to the total acid content. When an additional diacid is employed at a concentration greater than about 10 mole percent, particularly at about 25 mole percent or greater with respect to the total diacid content, the resulting polyamide exhibits a longer set time prior to becoming completely non-blocking. Accordingly, it is often desirable to add an additional ingredient to increase the rate of set as described in further embodiments as follows.

Additionally, other water soluble polyamides contribute comparable humidity and blocking resistance provided a chain terminator is employed during the reaction and/or the polyamide is further combined with at least one additional ingredient including waxes, solid tackifiers, monocarboxylic acids, and crystalline polymers. In these embodiments, the polyamide is produced by reacting at least one polyoxyalkylene diamine with dicarboxylic acid or an ester thereof, said polyoxyalkylene diamine having the formula:

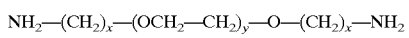

wherein X ranges from 2 to 3 and Y ranges from 1 to 2.

Chain terminators include monoacids and/or monoamines and are useful in an amount less than about 5 wt-%, preferably from about 0.5 wt-% to about 2.5 wt-% based on total acid weight to control the molecular weight. Representative examples of useful monocarboxylic acids include stearic acid, benzoic acid and montannic acid such as Wax S available from Hoechst Celanese. In the absence of a chain terminator, the resulting polyamide, particularly those taught by Speranza in U.S. Pat. Nos. 5,053,484, 5,086,162, 5,324, 812, and 5,118,785 are deficient in at least one property including exhibiting a high melt point, slow rate of set, high viscosity, poor humidity resistance and/or poor blocking resistance.

In addition or in the alternative, the polyamide component may be combined with at least one ingredient selected from the group consisting of waxes, tackifiers, crystalline polymers, monocarboxylic acids and mixtures thereof The monocarboxylic acids and monoamines have been found to be useful not only as a reactant as previously described but also as an ingredient to be added after the polyamide is formed.

NP-2126 as well as other grades of water soluble or water dispersible polyamides are commercially available from H. B. Fuller Company (St. Paul, Minn.).

Other crystalline water sensitive polymers surmised to be suitable for use as the thermoplastic polymer in the invention include polyethylene oxide available from Union Carbide (Danbury, Conn.) and crystalline polyesters. Water sensitive polymers that can be synthesized to possess similar physical properties such as viscosity and extent of crystallinity to that of the exemplary polyamides are believed to be particularly useful.

Amorphous water sensitive thermoplastic polymers contemplated for use in the present invention include such polymers as polyvinyl alcohol (PVOH) available from Nippon Grohsei (Japan) such as Grohseran L-301 and Grohseran L-302 and Unitika available from Unitaka Ltd. (Japan); polyvinyl pyrrolidone (PVP) available from BASF (Mount Olive, N.J.) and ISP (Wayne, N.J.); polyvinyl pyrrolidone/vinyl acetate copolymer (PVP/VA) and polyvinyl pyrrolidone/acrylic acid such as Acrylidone, both available from ISP; polyethyloxazoline available from The Dow Chemical Company (Freeport, Tex.) under the tradename PEOX and from PCI Incorporated (Tucson, Ariz.) under the tradename Aquazol, polyvinyl methyl ether available from Amoco Chemical Co. under the tradename Amobond, linear polyesters, polyacrylamide and preferably water dispersible polyesters and copolyesters (Eastman AQ) and amorphous water soluble and water dispersible polyamides.

One particularly preferred class of amorphous water sensitive thermoplastic polymers is water dispersible polyesters and copolyesters available from Eastman Chemical Company (Kingsport, Tenn.) under the tradename Eastman AQ. These water dispersible polymers are linear polyesters or branched copolyesters containing sulfonomer. Such polymers are saline and body fluid insoluble, yet dispersible in tap water. The Tg of the branched water dispersible copolyesters ranges from about −5° C. to 7° C., whereas the linear polyesters have a Tg from about 30° C. to about 60° C. Commercial examples of solid thermoplastic linear water dispersible polyesters include AQ 35S (7,000 Mn), AQ 38S (10,000 Mn), and AQ 55S (8,000 Mn).

Preferred water dispersible copolyesters are those which are branched and exhibit an intrinsic viscosity of about 0.6 IV (Eastman AQ-14000) or less, more preferably about 0.4 IV (Eastman AQ-1950) or less, even more preferably about 0.3 IV (Eastman AQ-1350) or less, and most preferably, particularly in combination with other higher molecular weight polymers, 0.2 IV (Eastman AQ-1045) or less. In terms of molten viscosity, these ranges correlate to a Brookfield viscosity ranging from about 5,000 to about 40,000 cPs. Information relating to the chemical synthesis of the branched polyesters may be found in U.S. Pat. Nos. 5,543,488 and 5,552,495, incorporated herein by reference. Lighter color and low odor modifications of such water dispersible copolyester are also contemplated, particularly for disposable absorbent articles in which odor and color tend to be important characteristics.

The thermoplastic composition of the present invention may employ a "conventional" thermoplastic polymer that is not breathable, water sensitive, nor biodegradable, provided the polymer is sufficiently diluted with plasticizers, waxes, and tackifying resins which contribute breathability. Such conventional thermoplastic polymers may be amorphous or crystalline and are typically polar to insure compatibility with the desired diluents.

Representative examples include ethylene-vinyl acetate copolymers containing about 12% to about 50% vinyl acetate such as Elvax 40 (40% vinyl acetate (VA), 55 melt index (MI), and Elvax 150 (33% VA, 44% MI), ethylene acrylic acid, ethylene methyl acrylate and ethylene n-butyl acrylate copolymers and polyamide polymers such as those available from H. B. Fuller Company (St. Paul, Minn.) and from Union Camp (Savannah, Ga.) as Unirez, and polyester polymers having low WVTR's available from Hüls as Vestamelt or EMS-Chemie (Sumter, S.C.) as Griltex. Other polymers that are typically too low in molecular weight to employ as the base polymer include polyesterurethane polymers such as Pearlstick, available from Aries Technologies (Dury, N.H.) and polyetherurethane polymers such as Estane, available from B. F. Goodrich Specialty Chemicals (Cleveland, Ohio).

Biodegradable polymers include thermoplastic materials that are photodegradable, microbiologically and hydrolytically degradable. Representative examples include polylactic acid, polylactide, poly (hydroxybutyrate), poly (hydroxybutyrate/hydroxyvalerate), polycaprolactone, and others.

In addition to the thermoplastic polymer, the breathable thermoplastic composition of the present invention comprises at least one diluent at an amount ranging from about 10 wt-% to about 90 wt-%. The amount of diluent employed depends on the desired properties. Typically, however, higher concentrations of diluents may be employed with high molecular weight polymers, for example those having a melt index (MI) of less than 30 g/10 min, and preferably less than about 10 g/10 min. Alternatively lower concentrations of diluents are employed in combination with higher melt index (low molecular weight) thermoplastic polymers.

The thermoplastic composition of the present invention preferably comprises a plasticizer as a diluent in an amount up to about 90 wt-% and preferably in an amount ranging from about 10 wt-% to about 50 wt-%. At high plasticizer concentrations, for example greater than about 50 wt-%, the plasticizer is preferably breathable. Breathable plasticizers also typically contain low reactivity oxygen linkages.

Compatible plasticizers are typically polar in nature including a variety of liquid plasticizers including phthalate plasticizers such as dioctyl phthalate and butyl benzyl phthalate, alkyl benzyl phthalate, and benzyl phthalate (e.g., Santicizer 160, 261, 278 respectively from Monsanto, St. Louis, Mo.); liquid polymers such as liquid polyesters (e.g., Dynacol 720 from Hüls), liquid polymeric plasticizer available from C P. Hall, Chicago, Ill. and liquid epoxidized Kraton; benzoate plasticizers such as 1,4-cyclohexane dimethanol dibenzoate (e.g., Benzoflex 352 from Velsicol, Rosemont, Ill.), diethylene glycol/dipropylene glycol dibenzoate (e.g., Benzoflex 50 from Velsicol), dipropylene glycol dibenzoate (e.g., Benzoflex 9-88 from Velsicol), polypropylene glycol dibenzoate (e.g., Benzoflex 400 from Velsicol), and diethylene glycol dibenzoate where the mole fraction of hydroxyl groups which have been esterified ranges from 0.5 to 0.95 (e.g., Benzoflex 2-45 High Hydroxyl also from Velsicol); phosphite plasticizers such as t-butyl diphenyl phosphate (e.g., Santicizer 154 from Monsanto); polyethylene glycol having a molecular weight below about 2000 (e.g., Carbowax 1000 from Union Carbide) and derivatives of polyethylene glycol including Pycal 94, the phenyl ether of PEG available from ICI (Wilmington, Del.); ethoxylated bis phenol A (e.g., Macol 206 EM from PPG Industries, Pittsburgh, Pa.); dionyl phenol ethyoxylates (e.g., Surfonic DNP from Huntsman Chemical Corp.); liquid rosin derivatives having Ring and Ball softening points below about 60°

C. such as methyl ester of hydrogenated rosin (e.g., Hercolyn D from Hercules, Wilmington, Del.); toluene sulfonamide (Uniplex 214 from Unitex Chemical Corp, Greensboro, N.C.); as well as vegetable and animal oils such as glycerol esters of fatty acids and polymerizable products thereof.

Further, a variety of monoalcohols, diols and polyols may be employed as a plasticizing diluent in the breathable compositions of the present invention. Useful polyols include polyethers, polyesteramides, polythioethers, polycarbonates, polyacetals, polyolefins, and polysiloxanes. Preferred polyols are low in molecular weight and include various grades of castor oil, ricinoleate polyols (highly refined castor oil) and derivatives thereof; ethylene glycol, propylene glycol, diethylene glycol, dipropylene glycol, 1,4-butanediol, 1,6-hexanediol as well as higher functional polyols having more than two hydroxyl groups per molecule such as glycerol, trimethylolpropane, 1,2,4-butanetriol, 1,2, 6-hexanetriol, and mixtures thereof.

Castor oil, also known as ricinus oil, is a triglyceride (ester) of fatty acids derived from the seed of the castor plant. Approximately 90% of the fatty acid content is ricinoleic acid, an 18 carbon acid having a double bond in the 9-10 position and a hydroxyl group on the $12^{th}$ carbon. The remainder of castor oil is made up of dihydroxystearic acid (0.7%), palmitic acid (1%), stearic acid (1%), oleic acid (3%), linoleic acid (4.2%), linolenic acid (0.3%) and eicosanoic acid (0.3%). Castor oil is available in a variety of grades from several suppliers.

The most preferred plasticizers are those that contain sufficient ether, hydroxyl, and/or polyol linkages to enhance the breathability of the formulation.

A variety of liquid surfactants may be employed in the breathable composition of the present invention as a plasticizing diluent. Suitable surfactants include nonionic, anionic, and silicone surfactants. Exemplary nonionic surfactants are:

Ethoxylates of (i) C sub 1-C sub 18, preferred C sub 8-C sub 9 alkyl or dialkyl phenols, such as those sold under the tradenames Macol DNP-10, available from PPG Industries, Gurnee, Ill., a 10 mole ethoxylate of dinonyl phenol, and Triton X-100, available from Union Carbide, a 10 mole ethoxylate of octyl phenol; (ii) alkyl C sub 8-C sub 60 mono-alcohols, such as those sold under the tradenames Surfonic L-12-8, an 8 mole ethoxylate of dodecanol, available from Huntsman Chemical Co., and Unithox 480, a 38 mole ethoxylate crystalline surfactant available from Petrolite Specialty Polymers Group, Tulsa, Okla.; and (iii) propylene oxide polymers, such as those sold under the tradename Pluronic, which are ethylene oxide/propylene oxide block copolymers having Mn of 200 to 3000 available from BASF; and benzoates formed by partial ondensation of benzoic acid with hydrophilic di or mono-ols having less than 1000 Mn, such as the product of condensing about three equivalents of benzoic acid with four equivalent of diethylene glycol, commercially available as XP 1010 from Velsicol Chemical. A preferred nonionic surfactant blend is Atmer 685, available from ICI Surfactants (Wilmington, Del.).

Suitable anionic surfactants are: C sub 8-C sub 60 alkyl ethoxylate sulfonates, (CH sub 3 —(CH sub 2) sub 11-14 —(O—CH sub 2 CH sub 2) sub 3 —SO sub 3-Na sup +, such as, Avenel S30, available from PPG Industries; alkyl C sub 8-C sub 60 sulfonates, such as, Rhodapon UB (C sub 12 —SO sub 3 sup-Na sup+) available from Rhone Poulenc; sorbitan ester available as Atmer 100 from ICI Surfactants; and alkyl/aromatic sulfonates, such as those sold under the tradename Calsoft.

Suitable silicone surfactants are ethoxylates or propoxylates of polydimethyl siloxane, having a number average molecular weight of 500 to 10,000, preferably 600 to 6000, such as are sold under the tradenames Silwet L-77, L-7605, and L-7500 available from OSi Specialties, Danbury, Conn.; and product 193 from Dow Corning.

The preferred surfactants exhibit a relatively low molecular weight that tends to improve the compatibility in the adhesive formulations. The maximum acceptable molecular weight depends on the type of surfactant and the solubility and/or compatibility with the polymer employed in the formulation.

The breathable thermoplastic composition of the present invention may comprise one or more tackifying resins particularly if the composition is intended to adhere one or more substrates (in addition to forming a barrier layer). The tackifying resins useful herein are generally polar in nature and have a Ring & Ball softening point greater than 60° C. and include any compatible resins or mixtures thereof such as natural and modified rosins such as gum rosin, wood rosin, tall oil rosin, distilled rosin, hydrogenated rosin, dimerized rosin, and polymerized rosin; rosin esters such as glycerol and pentaerythritol esters of natural and modified rosins such as, for example, the glycerol ester of pale, wood rosin, and the glycerol ester of hydrogenated rosin, the glycerol ester of polymerized rosin, and the pentaerythritol ester of hydrogenated rosin, and the phenolic-modified pentaerythritol ester of rosin; phenolic modified terpene or alpha methyl styrene resins as well as the hydrogenated derivatives thereof such as the resin product resulting from the condensation in an acidic medium of a bicyclic terpene and a phenol.

Representative examples of preferred tackifiers include Foral NC, Kristalex 3100 (100° C. melt point) and 3085 (85° C. melt point) and Endex, hydrogenated alpha methyl styrene resins available from Hercules (Wilmington, Del.); non-ionic materials such as Foral AX also from Hercules, alpha methyl styrene phenolics such as Uratak 68520 from DSM Resins (Panama City, Fla.), rosin esters such as Unitac R100L available from Union Camp, terpene phenolic tackifiers such as Nirez 300, V2040 and 2019 available from Arizona Chemical (Panama City, Fla.).

The breathable thermoplastic composition of the present invention may further comprise a wax in an amount up to about 30 wt-%, more preferably at an amount ranging from about 3 wt-% to about 20 wt-%, and most preferably from about 5 wt-% to about 15 wt-%. Waxes are particularly useful for decreasing the surface tack of the barrier film layer. Waxes useful herein are preferably polar in nature. Polar waxes are those which contain at least one polar functional group such as hydroxyl, amide, sulfone, phosphate, sulfonamide, urethane, carboxylate acid, amine, and carbonate. The concentration of the functional group is present in an amount greater than about $2 \times 10^{-3}$ equivalents per gram and preferably greater than $3.5 \times 10^{-3}$ equivalents per gram. The molecular weight of waxes ranges from about 200 g/mole to about 1000 g/mole. Representative examples including 12-hydroxystearamide, N-(2-hydroxy ethyl 12-hydroxystearamide and N,N'ethylene bis 12-hydroxystearamide (PARICIN 220 and PARICIN 285 respectively, from CasChem, Bayonne, N.J.), stearamide (Kemamide S from Witco, Memphis, Tenn.), glycerin monostearate, sorbitan monostearate, and 12-hydroxy stearic acid. Also useful alone or in combination with the above are less polar waxes such as N,N'-ethylene-bis stearamide (Kemamide W-40 from Witco), linear aliphatic long chain alcohols (Unilin 425 from Petrolite, Tulsa, Okla.), hydrogenated castor oil (castor wax), oxidized synthetic waxes, and functionalized waxes such as oxidized homopolymers and oxidized polyethylene waxes (Petrolite E-1040). The Applicants have found that polar waxes having a melt point greater than 70° C., preferably greater than about 110° C., and more preferably about 140° C. or greater, are particularly advantageous.

A variety of other polymers, tackifiers and additives such as antioxidants (Irganox 1010), pigments and fillers, particularly hydrophilic fillers such as starch or cellulose esters and acetates, may be employed in an amount up to about 10 wt-% provided such materials do not detract from the humidity resistance, blocking resistance and speed of moistenability contributed by the blend of crystalline water sensitive polymer with amorphous water sensitive polymer.

Radiation curable compositions for use in the invention are those compositions that can be applied as a continuous layer, attain their desired film properties by virtue of being crosslinked upon exposure to a radiant energy source such as electron beam (EB) or ultraviolet (UV). Similarly, as in the case of compositions which are not radiation responsive, the breathability is contributed by having a sufficient amount of oxygen linkages dispersed throughout the film layer such that after curing the film/film layer has a WVTR of at least 100 g/m$^2$/day.

Whether or not the resulting film layer is breathable, curable compositions typically possess low initial viscosities and can develop high film strengths by the crosslinking during curing. For such embodiments exhibiting sufficient film strength, the layer may be self-supporting. Hence, the composition need not be coated onto a reinforcement material. Hence, in the case of the preferred coating method as described in U.S. Pat. No. 5,827,252, the substrate being coated may be a release coated roller rather than a material such as a nonwoven that becomes part of the finished article.

Radiation curable compositions that find utility for breathable films/barrier layer applications include acrylated polyesters commercially available from H.B. Fuller Company under the tradename SolarCure as well as acrylated branched polyesters available as Dynacoll A from Creanova. The branched structure results in amorphous character. The hydroxyl containing polyesters are subsequently reacted with acrylic functional adducts as described in U.S. Pat. No. 4,822,829 yielding an acrylated polyester which are responsive to both UV and EB radiation. In the case of UV curing, a photoinitiator is also required.

Depending on the molecular weight (Mn), which is typically below 15,000 atomic mass units (amu's), the compounded or neat acrylated polyesters can be applied at temperatures ranging from 60° C. to 120° C. Exposure to a radiant energy source results in an immediate cure that increases the molecular weight and intramolecular crosslinking.

The acrylated polyesters have been found to exhibit high WVTR even after crosslinking. Several of the Solarcure grades of acrylated polyester are pressure sensitive in a neat, unformulated state allowing them to be amenable to creating fluid impermeable barrier film layers that simultaneously serve an adhesive function. In the case of feminine napkins, bandages, etc., this would eliminate the need to have a separate barrier layer coated with an adhesive. The pressure sensitivity or film properties can be enhanced by the addition of other polymers, tackifying resins, and plasticizers. Alternatively, for applications in which pressure sensitivity is undesirable, other grades of acrylated polyesters may be employed or the surface tack may be diminished with compounding.

Additional radiation curable ingredients that exhibit utility for radiation curable breathable films/film layers include the Kraton KLP (Kraton Liquid Polymers available from Shell) and acrylic polymers such as Acrynol DS 3429 and DS 3458, available from BASF. The Kraton KLP contains reactive epoxy linkages and is compounded with hydroxyl terminated polymers and photoinitiator to yield a photoreactive composition, whereas the Acrynol contains bound photoinitiator in some degree of reactive unsaturation. These polymers can also be formulated into compositions that are useful for creating breathable films/film layers upon irradiation to provide the desired properties.

The invention is further illustrated by the following non-limiting examples.

EXAMPLES

Test Methods

Following is a list of the tradename, chemical description and supplier or ingredients employed in the examples that are not previously described.

| Tradename | Description | Supplier |
|---|---|---|
| Polymers | | |
| Hytrel 8171 | butylene/poly(alkylene ether)-phthalate | Dupont |
| Joncryl 587 | styrene acrylic polymer | Johnson & Son, Inc. (Racine, WI) |
| LP BAK 44-004 | biodegradable polyester polyamide | Bayer AG |
| Nucrel 699 | ethylene methacrylic acid copolymer | Dupont |
| Nucrel 010 | ethylene methacrylic acid copolymer | Dupont |
| Nucrel 535 | ethylene methacrylic acid copolymer | Dupont |
| PEBAX MV 1074 | polyether block amide | Elf Atochem (Philadelphia, PA) |
| Tackifying Resin | | |
| Nevex 100 | modified hydrocarbon tackifying resin | Neville (Pittsburg, PA) |
| Synthetic Resin AP | | Huls (Piscataway, NY) |
| Plasticizers | | |
| Dontocol DHE | 2,4-imidazolidinedione,1,3-bis (2-hydroxyethyl)-5,5-dimethyl | Lonza (Fair Lawn, NJ) |
| Riticizer 8 | n-ethyl o/p toluene sulfonamide | RitChem (Pleasantville, NY) |
| Terathane 2000 | polyether glycol (2000 molecular wt) | Dupont |
| Uniflex 314 | adipic acid polymer with diol | Union Camp (Jacksonville, FL) |

Tables 1–3 depict the WVTR of various impermeable barrier layers of the present invention formed from relatively low viscosity breathable thermoplastic compositions. Table 1 depicts the compositions and water vapor transmission rates of Examples 1–4. The ingredients of column 1 were combined at the weight ratios of column 2. The compositions were slot coated molten with a 4 mm shim gap producing a 40 to 50 μm continuous coating. Examples 1, 3 & 4 employ a breathable thermoplastic polymer combined with a plasticizing diluent, whereas Example 2 employs a compounded water sensitive thermoplastic composition.

TABLE 1

| Example #-Ingredients | Weight Ratio | WVTR |
|---|---|---|
| Ex. 1-Pebax MV 1074/Castor oil AA | 40/60 | 653 |
| Ex. 2-NP-2246 | | 215 |
| Ex. 3-Pebax 2533/Castor oil AA | 50/50 | 330 |
| Ex. 4-Pebax 2533/PEG 1000/Castor oil AA | 50/20/30 | 920 |

Tables 2A and 2B depict the composition, compatibility, film tack, water sensitivity of various breathable thermoplastic compositions based on water sensitive thermoplastic polymers. In each of the examples, Eastman AQ-1350 was blended with the ingredient(s) of column 1 at the weight-% ratios indicated in column 2. The first number expressed in the weight-% ratio of column 2 refers to the amount of Eastman AQ-1350.

TABLE 2A

| Example # - Modifying Ingredient | Weight Ratio | Compatibility Hot | Compatibility Cold | Film Tack | Water Sensitivity | Bleeding |
|---|---|---|---|---|---|---|
| Ex. 5 - Nevex 100 | 30/70 | No | Ok (sl cloudy) | 1 | 3 | |
| Ex. 6 - Nevex 100 | 50/50 | No | Ok (sl cloudy) | 2 | 3 | |
| Ex. 7 - Nevex 100 | 70/30 | ? | no | 2 | 3 | |
| Ex. 8 - Nirez 2019 | 30/70 | Ok | ok | 1 | 3 | |
| Ex. 9 - Nirez 2019 | 50/50 | Ok | ok | 1 | 3 | |
| Ex. 10 - Nirez 2019 | 70/30 | Ok | ok | 1 | 3+ (10 min) | |
| Ex. 11 - Kristalex 3100 | 70/30 | No | Cloudy | 1 | 1 | |
| Ex. 12 - Foral AX | 70/30 | Ok | ok | 3 | 1 | |
| Ex. 13 - Peox 5 | 50/50 | Ok | ok | 2 | 1 | |
| Ex. 14 - Peox 200 | 50/50 | Marginal | Looks ok | 2 | 1 | |
| Ex. 15 - NP-2126 | 50/50 | Ok | Ok (sl cloudy) | 1 | 1 | |
| Ex. 16 - Nucrel 699 | 50/50 | No | no | 1 | 1 | |
| Ex. 17 - Joncryl 587 | 50/50 | Ok | ok | 1 | 1 | |
| Ex. 18 - Aquazol 5/NP-2126 | 50/50 | Ok | ok | 1 | 1 | |
| Ex. 19 - Pycal 94 | 80/20 | Ok | ok | gummy | 1 | 3 |
| Ex. 20 - Pycal 94 | 90/10 | | | | 1 | |
| Ex. 21 - Atmer 100 | 80/20 | Ok | Cloudy | | 1 | 3 |
| Ex. 22 - Santicizer 160 | 80/20 | Ok | ok | 4 | 1 | 3 |
| Ex. 23 - Santicizer 160 | 90/10 | Ok | ok | 4 | 1 | |
| Ex. 24 - Santicizer 261 | 80/20 | Ok | ok | 3–4 | 1 | 3 |
| Ex. 25 - Santicizer 261 | 90/10 | Ok | ok | 3 | 1 | |
| Ex. 26 - Santicizer 278 | 80/20 | Ok | ok | 4 | 1 | 3 |
| Ex. 27 - Santicizer 278 | 90/10 | Ok | ok | 4 | 1 | 2 |
| Ex. 28 - Dantocol DHE | 80/20 | Ok | ok | 4 | 1 | 3 |
| Ex. 29 - Uniflex 314 | 80/20 | Ok | ok | 4 | 1 | 3 |
| Ex. 30 - Uniflex 314 | 90/10 | Ok | ok | 4 | 1 | 2 |
| Ex. 31 - Castor Oil AA - Standard | 80/20 | Ok | ok | 4 | 1 | 3 |
| Ex. 32 - Castor Oil AA - Standard | 90/10 | Ok | ok | 3–4 | 1 | 3 |
| Ex. 33 - Benzoflex 352 | 80/20 | Ok | Crystallizes | 1 | 1 | 1 |
| Ex. 34 - Benzoflex 352 | 95/5 | Ok | ok | 3 | 1 | 1 |
| Ex. 35 - Peox 5 | 50/50 | Ok | ok | 2 | 1 | |
| Ex. 36 - Peox 200 | 50/50 | Marginal | ok | 2 | 1 | |

TABLE 2B

Three Component Blends

| Example # - Modifying Ingredient | Weight Ratio | Compatibility Hot | Compatibility Cold | Film Tack | Water Sensitivity |
|---|---|---|---|---|---|
| Ex. 37 - Nirez 2019/Sant 261 | 60/30/10 | Cloudy | 2 | 2 | 3 |
| Ex. 38 - Nevex 100/Sant 261 | 60/30/10 | Grainy/not com | 2 | 2 | 3 |
| Ex. 39 - Nirez 2019/Pycal 94 | 60/30/10 | Ok | Cloudy | 3 | 1 |
| Ex. 40 - Nevex 100/Pycal 94 | 60/30/10 | Grainy | sl cloudy | 3+ | 1 |
| Ex. 41 - Aquazol 5/NP-2126 | 50/50 | Ok | Ok | 1 | 1 |
| Ex. 42 - NP-2126/HM0814 | 50/50 | Ok | sl cloudy | 1+ | 1 |
| Ex. 43 - NP-2126/HL-6090 | 50/50 | Ok | sl cloudy | 2 | 1 |
| Ex. 44 - NP-2126/HL-3296 | 50/50 | No | sl cloudy | 1 | Disintegrates |

Table 3 depicts the composition, compatibility, film tack, and water sensitivity of various breathable thermoplastic compositions comprising a breathable thermoplastic polymers and a diluent. In each of the examples, PEBAX 2533 was blended with the ingredient(s) of column 1 at the weight-% ratios indicated in column 2. The first number expressed in the weight-% ratio of column 2 refers to the amount of PEBAX 2533.

TABLE 3

| Example #<br>Modifying Ingredient | Weight<br>Ratio | Compatibility<br>Hot | Compatibility<br>Cold | Film<br>Tack | Water<br>Sensitivity | Bleeding |
|---|---|---|---|---|---|---|
| Ex. 45 - Ritcizer 8 | 50/50 | Ok | Ok | 2 | 3 | No |
| Ex. 46 - Benzoflex 50 | 50/50 | Ok | Ok | 2 | 3 | No |
| Ex. 47 - Castor Oil | 50/50 | Ok | Ok | 2 | 3 | No |
| Ex. 48 - Peox 50 | 50/50 | ok | Ok | 2 | 3 | No |
| Ex. 49 - AQ-1045 | 50/50 | no | Ok | — | — | — |
| Ex. 50 - Benz 50/AQ-1045 | 33/33/33 | ok | Cloudy | Low tack | minimal | No |
| Ex. 51 - Benz 50/AQ/Foral AX | 25/25/25/25 | ok | Almost clear | Tacky | no | No |
| Ex. 52 - Castor Oil/AQ-1045 | 33/33/33 | ok | Cloudy/smooth | | not very | No |
| Ex. 53 - Castor Oil/AQ/Foral AX | 25/25/25/25 | ok | | very tacky | not very ws | No |
| Ex. 54 - Peox 50/Ritcizer 8 | 33/33/33 | no | — | — | — | — |
| Ex. 55 - AQ-1045/Ritcizer 8 | 33/33/33 | no | — | — | — | — |

Example 56

2000 g of Hytrel 8171 was combined molten with 800 b of Benzoflex 9-88. The viscosity of the blend was 96,500 cPs at 177° C. and 51,250 cPs at 163° C.

Example 57

75 g of a mixture of 54% Terathane 2000 (40.5 g) and 45% PEBAX 2533 (33.75 g) was combined with 75.0 g of PEBAX 2533. The final mixture contained about 72.5 wt-% PEBAX 2533 and about 28 wt-% Terathane 2000. The composition exhibited good cohesive strength and good compatibility. The cooled sample did not exhibit any physical phase separation over 3 days and a molten sample did not phase separate after 8 hours at 177° C. The viscosity of the composition was 11,600 cPs at 177° C. and 25,450 at 300° F.

Examples 58–62

The following EVA based compositions were prepared and tested as follows:

| | Ex. 58 | Ex. 59 | Ex. 60 | Ex. 61 | Ex. 62 |
|---|---|---|---|---|---|
| Wt-% | | | | | |
| Elvax 40 | 50 | 50 | 50 | 50 | 25 |
| Elvax 50 | | | | | 25 |
| Kristalex 3085 | 25 | 35 | | | |
| Kristalex 3100 | | | | | 35 |
| Synthetic Resin AP | | | 25 | 35 | |
| Terathane 2000 | 24 | 14 | 24 | 14 | 14 |
| Irganox 1010 | 0.5 | 0.5 | 0.5 | 0.5 | 0.5 |
| Irganox 1076 | 0.5 | 0.5 | 0.5 | 0.5 | 0.5 |
| Viscosity (cPs) | | | | | |
| at 350° F. | 17,275 | 19,125 | | | |
| at 325° F. | 25,800 | 29,150 | | | |
| at 300° F. | 39,600 | 46,250 | | | |
| at 275° F. | 64,500 | 78,300 | | | |
| at 250° F. | 114,750 | | | | |

There was no evidence of the Terathane 2000 bleeding out. Additionally, Examples 58 and 59 were repeated replacing the Kristalex 3085 with Kristalex 3100 (100° C. melt point) contributing a lower tack level to the film with respect to the 85° C. melt point resin.

Examples 63–72

The following methacrylic acid based compositions were prepared and tested as follows:

| | Ex. 63 | Ex. 64 | Ex. 65 | Ex. 66 | Ex. 67 |
|---|---|---|---|---|---|
| Wt (g) | | | | | |
| Nucrel 599 | 300 | 50 | | 98 | 98 | 34 wt-% |
| Terathane 2000 | 100 | 50 | | 50 | 50 | |
| Nucrel 010 | | | 75 | 50 | | |
| Elvax 40 | | | | | 50 | |
| Example 58 | | | | | | 66 wt-% |
| Irganox 1010 | 1.0 | 1.0 | | 2.0 | 2.0 | |
| Viscosity (cPs) | | | | | | |
| at 375° F. | | | | 35,000 | | |
| at 350° F. | | | | 52,800 | | |
| at 325° F. | | | | 123,500 | | |

| | Ex. 68 | Ex. 69 | Ex. 70 | Ex. 71 | Ex. 72 |
|---|---|---|---|---|---|
| Wt (g) | | | | | |
| Nucrel 535 | 148 | | | | |

-continued

| | | | |
|---|---|---|---|
| Nucrel 699 | | 148 | 138 |
| Terathane 2000 | 50 | 50 | 60 |
| Kristalex 3100 | | | |
| Irganox 1010 | 2.0 | 2.0 | 2.0 |
| Viscosity (cPs) | | | |
| at 400° F. | 71,000 | | |
| at 375° F. | | | |
| at 350° F. | | 52,200 | 40,300 |
| at 325° F. | | 121,750 | 81,650 |
| at 300° F. | | | 209,250 |

Example 70 was coated onto nonwoven with the method described in U.S. Pat. No. 5,827,252 issued Oct. 27, 1998 at a speed of 75 to 100 ft/min. The composition was melted at a temperature of 350° F. (177° C.) and coated with a slot coater employing a die temperature of 320–350° F. (160° C.–177° C.). A 0.8 and 1.0 mil thick barrier film layer was produced. The 1.0 mil film was found to have a WVTR of 261 grams/m²/day in accordance with ASTM 1249.

What is claimed is:

1. A composition selected from the group consisting of:
   a) a noncuring thermoplastic composition comprising ethylene methacrylic acid copolymer and at least one diluent; and
   b) a radiation curable composition;
   wherein said composition has a water vapor transmission rate of at least about 100/m²/day according to ASTM E 96 for a 50 μm film thickness.

2. The composition of claim 1 wherein the water vapor transmission rate is at least about 200 g/m²/day.

3. The composition of claim 1 wherein the water vapor transmission rate is at least about 400 g/m²/day.

4. The composition of claim 1 wherein the water vapor transmission rate is at least about 800 g/m²/day.

5. The composition of claim 1 wherein the water vapor transmission rate is at least about 1000 g/m²/day.

6. The composition of claim 1, wherein the thermoplastic composition further comprises a thermoplastic polymer selected from the group consisting of breathable polymers, water sensitive polymers, biodegradable polymers, conventional polymers and mixtures thereof.

7. The composition of claim 1 wherein said thermoplastic composition further comprises polyether block amide.

8. The composition of claim 7 wherein the polyether block amide has a water vapor permeability of at least 1500 g/m²/24 hours for a 30 micron film thickness.

9. The composition of claim 1 wherein the diluent is a plasticizer.

10. The composition of claim 1 wherein the plasticizer is selected from the group consisting of castor oil, polyethylene glycol and mixtures thereof.

11. A disposable article comprising a body fluid impermeable barrier layer comprising a composition selected from the group consisting of
   a) a noncuring thermoplastic composition comprising at least one thermoplastic polymer and at least one diluent, and
   b) a radiation curable composition,
   wherein said composition has a water vapor transmission rate of at least about 100/m²/day according to ASTM E 96 for a 50 μm film thickness.

12. The article of claim 11 wherein said composition has a water vapor transmission rate is at least about 200 g/m²/day.

13. The article of claim 11 wherein said composition has a water vapor transmission rate is at least about 400 g/m²/day.

14. The article of claim 11 wherein said composition has a water vapor transmission rate is at least about 800 g/m²/day.

15. The article of claim 11 wherein said composition has a water vapor transmission rate is at least about 1000 g/m²/day.

16. The article of claim 11 wherein said thermoplastic composition further comprises polyether block amide.

17. The article of claim 11 wherein the diluent is a plasticizer.

18. The article of claim 11 wherein the plasticizer is selected from the group consisting of castor oil, polyethylene glycol and mixtures thereof.

19. An article selected from the group consisting of footwear, rainwear, medical garments, tarpaulins, and tents having a fluid impermeable barrier layer comprising a composition selected from the group consisting of
   a) a noncuring thermoplastic composition comprising at least one thermoplastic polymer and at least one diluent, and
   b) a radiation curable composition,
   wherein said composition has a water vapor transmission rate of at least about 100/m²day according to ASTM E 96 for a 50 μm film thickness.

20. The article of claim 19 wherein said composition has a water vapor transmission rate is at least about 200 g/m²/day.

21. The article of claim 19 wherein said composition has a water vapor transmission rate is at least about 400 g/m²/day.

22. The article of claim 19 wherein said composition has a water vapor transmission rate is at least about 800 g/m²/day.

23. The article of claim 19 wherein said composition has a water vapor transmission rate is at least about 1000 g/m²/day.

24. The article of claim 19 wherein said thermoplastic composition further comprises polyether block amide.

25. The article of claim 19 wherein the diluent is a plasticizer.

26. The article of claim 19 wherein the plasticizer is selected from the group consisting of castor oil, polyethylene glycol and mixtures thereof.

* * * * *

UNITED STATES PATENT AND TRADEMARK OFFICE
CERTIFICATE OF CORRECTION

PATENT NO. : 6,432,547 B1 Page 1 of 1
DATED : August 13, 2002
INVENTOR(S) : Mark S. Kroll and Greg J. Van Lith It is certified that error appears in the above-identified patent and that said Letters Patent is hereby corrected as shown below:

Column 2,
Lines 4 and 14, "Theological" should be -- rheological --

Column 13,
Line 58, "Elvax 50" should be -- Elvax 150 --
Line 33, "800 b" should be -- 800 g --

Signed and Sealed this

Twenty-second Day of April, 2003

JAMES E. ROGAN
*Director of the United States Patent and Trademark Office*